(12) United States Patent
Diaz et al.

(10) Patent No.: US 6,562,999 B2
(45) Date of Patent: May 13, 2003

(54) PROCESS FOR SEPARATION OF CRUDE NAPHTHALENE DICARBOXYLIC ACID USING REVERSE OSMOSIS

(75) Inventors: Zaida Diaz, Houston, TX (US); John B. Rodden, Houston, TX (US)

(73) Assignee: Mossi & Ghisolfi Overseas S.A. (LU)

( * ) Notice: Subject to any disclaimer, the term of this patent is extended or adjusted under 35 U.S.C. 154(b) by 0 days.

(21) Appl. No.: 10/042,606

(22) Filed: Jan. 9, 2002

(65) Prior Publication Data

US 2002/0123646 A1 Sep. 5, 2002

Related U.S. Application Data

(63) Continuation of application No. 09/643,354, filed on Aug. 22, 2000, now abandoned.
(60) Provisional application No. 60/151,577, filed on Aug. 30, 1999, provisional application No. 60/151,607, filed on Aug. 30, 1999, provisional application No. 60/151,498, filed on Aug. 30, 1999, provisional application No. 60/151,602, filed on Aug. 30, 1999, provisional application No. 60/151,603, filed on Aug. 30, 1999, provisional application No. 60/151,529, filed on Aug. 30, 1999, provisional application No. 60/151,489, filed on Aug. 30, 1999, provisional application No. 60/151,604, filed on Aug. 30, 1999, provisional application No. 60/151,606, filed on Aug. 30, 1999, provisional application No. 60/151,589, filed on Aug. 30, 1999, provisional application No. 60/151,497, filed on Aug. 30, 1999, provisional application No. 60/151,590, filed on Aug. 30, 1999, and provisional application No. 60/151,578, filed on Aug. 30, 1999.

(51) Int. Cl.[7] .................. C07C 51/347; C07C 51/42; C07C 51/15; C07C 63/38
(52) U.S. Cl. .................. 562/481; 562/480; 562/423; 562/485
(58) Field of Search .................. 562/423, 480, 562/481, 485

(56) References Cited

U.S. PATENT DOCUMENTS

| 2,823,231 A | 2/1958 | Raecke et al. |
| 2,849,482 A | 8/1958 | Raecke et al. |
| 3,631,096 A | 12/1971 | Kuper |
| 3,671,578 A | 6/1972 | Ogata et al. |
| 3,888,921 A | 6/1975 | Yamamoto et al. |
| 3,952,052 A | 4/1976 | Sherk |
| 5,175,354 A | 12/1992 | Mitamura et al. |
| 5,492,625 A * | 2/1996 | Wytcherley et al. |

FOREIGN PATENT DOCUMENTS

CA 864587 2/1971

OTHER PUBLICATIONS

The Dow Chemical Company, Product Information, 1998, FILMTEC Membranes, pp. 1–4.*
Kurita Water Industries JP 56020051 May 1981 Abstract.

* cited by examiner

Primary Examiner—Samuel L Barts
Assistant Examiner—Paul A. Zucker
(74) Attorney, Agent, or Firm—Renner Kenner Greive Bobak Taylor & Weber

(57) ABSTRACT

Disclosed is a process for purifying 2,6-naphthalene dicarboxylic acid produced by disproportionation and more efficiently recycling byproduct dipotassium salts which includes the steps of:

a) Contacting an aqueous solution containing the disalt of 2,6-NDA(2,6-K2NDA) with carbon dioxide to form as a precipitate the monopotassium salt of 2,6-NDA (KHNDA) and an aqueous solution containing 2,3-KHNDA, K2NDA, and potassium bicarbonate;

b) Disproportionating said monopotassium salt (KHNDA) to form 2,6-NDA and an aqueous solution containing K2NDA, and potassium bicarbonate;

c) Separating said 2,6-NDA and concentrating said aqueous solution containing K2NDA and potassium bicarbonate by reverse osmosis.

11 Claims, 1 Drawing Sheet

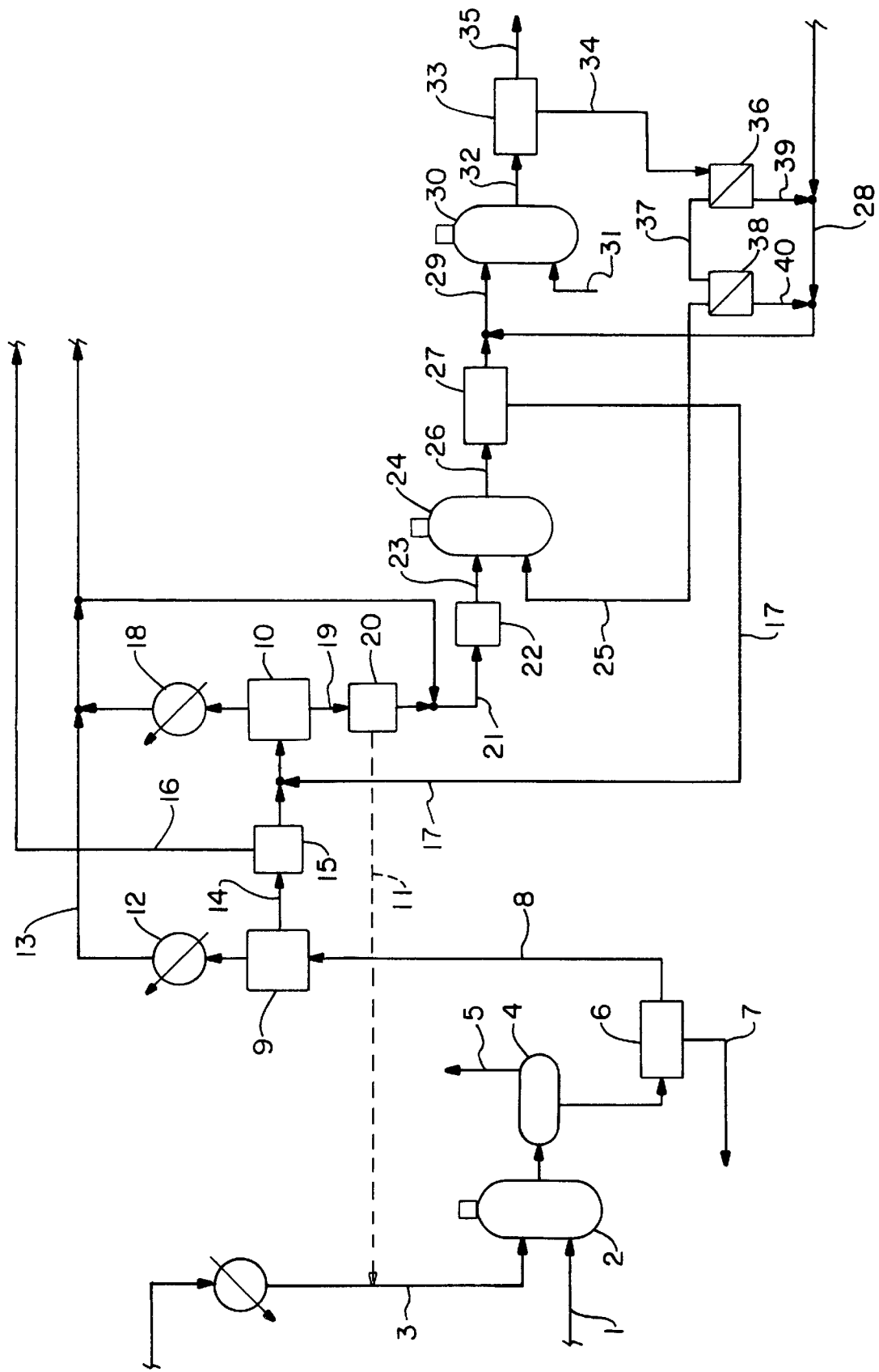

PROCESS FOR SEPARATION OF CRUDE NAPHTHALENE DICARBOXYLIC ACID USING REVERSE OSMOSIS

CROSS REFERENCE

This application is a continuation of U.S. Ser. No. 09/643,354 filed on Aug. 22, 2000, now abandoned, which claims the benefit of U.S. Ser. Nos. 60/151,577, 60/151,607, 60/151,498, 60/151,602, 60/151,603, 60/151,529, 60/151,489, 60/151,604, 60/151,606, 60/151,589, 60/151,497, 60/151,590 and 60/151,578 all filed on Aug. 30, 1999.

FIELD OF INVENTION

This invention is related to a process for the production of purified 2,6-naphthalene dicarboxylic acid (hereafter referred to as 2,6-NDA) from a crude 2,6-NDA disproportionation product. More particularly, this invention is related to a novel method of separating and recycling byproducts in a process for producing 2,6-NDA from a disproportionation product that utilizes reverse osmosis and is industrially advantageous.

BACKGROUND OF THE INVENTION

Aromatic carboxylic acids are highly useful organic compounds. They are useful as intermediates for the preparation of other organic compounds, and as monomers for the preparation of polymeric materials. In particular, the naphthalene carboxylic acids are used for preparing photographic chemicals and dyestuffs. Naphthalene dicarboxylic acids can also be used to prepare a variety of polyester and polyamide compositions. 2,6-NDA is a particularly useful aromatic carboxylic acid which can be reacted with ethylene glycol to prepare poly(ethylene-2,6-naphthalate). Polyesters prepared from 2,6-NDA have excellent heat resistance, gas barrier, and mechanical properties. Therefore, much research in the art has focused on methods of preparing 2,6-NDA. The production of 2,6-NDA from disproportionation product is described, for example, in U.S. Pat. Nos. 2,823,231 and 2,849,482.

Production of high purity 2,6-NDA from disproportionation product requires many process steps to separate impurities from the dipotassium salt of 2,6-NDA hereafter referred to as 2,6-K2NDA, which is the 2,6-NDA precursor. The impurities include naphthalene, zinc oxide, and several naphthalene mono- and dicarboxylic acid salts. This complexity results in numerous byproduct streams that must be recycled to make the process less costly.

There have been different approaches to the separation of the dialkali metal salt products of disproportionation reactions and conversion of them into 2,6-NDA.

In U.S. Pat. No. 2,823,231, the method used to separate the dialkali metal salts of 2,6-naphthalene dicarboxylic acid comprises dissolving the disproportionation conversion product mixture in water, filtering off insoluble impurities from the resulting solution, acidifying the filtrate with mineral or organic acid, such as sulfuric or hydrochloric acid, and separating the precipitated naphthalene-2,6-dicarboxylic acid from the acid solution. In U.S. Pat. No. 2,823,231 the dialkali metal salt of naphthalene 2,6-dicarboxylic acid formed is converted into free naphthalene 2,6-dicarboxylic acid by acidification of said dialkali metal salt with a strong mineral acid.

U.S. Pat. No. 2,849,482 teaches acidifying an aqueous solution of the crude reaction product of the disproportionation or converting the crude alkali metal salt directly into the dichloride or into esters of naphthalene-2,6-naphthalene dicarboxylic acid in accordance with known methods.

In U.S. Pat. No. 3,631,096, to Phillips, salts formed by the reaction can be transformed into the corresponding free acids by acidifying the solution with organic or inorganic acids or by introducing carbon dioxide into the solution at atmospheric or elevated pressure, and then separating the free acids from the acidified solution. The individual reaction products may be separated from each other and isolated in pure form by methods that are based upon their different solubilities or volatilities and may thereafter, if desired, be transformed into their derivatives. The salt mixture produced by the reaction may also be transformed directly into derivatives of the acids, for example, into their esters or halides, and these derivatives may be purified, if desired, by fractional distillation.

U.S. Pat. No. 3,671,578, to Teijin, discloses that the monoalkali salt of 2,6-naphthalene dicarboxylic acid is easily disproportionated when heated in water or water-containing organic solvent, to form free dicarboxylic acid and by-product dialkali salt, and the former acid is precipitated.

In U.S. Pat. No. 3,952,052, to Phillips, there is disclosed a process for separating a disproportionation reaction product by forming a slurry comprising alkali metal salts of aromatic polycarboxylic acid and dispersant and a gaseous effluent, and then lowering the pressure, flashing the dispersant, and recovering said alkali metal salts of said polycarboxylic acids as solids from said separation zone.

U.S. Pat. No. 3,888,921, to Teijin Ltd., discloses a method for purifying a dialkali salt of crude 2,6-naphthalene dicarboxylic acid comprising precipitating 40 to 97 mol percent of the dialkali 2,6-naphthalene dicarboxylate dissolved in an aqueous solution substantially as monoalkali salt of 2,6-naphthalenedicarboxylic acid while maintaining the pH of said aqueous solution at a value not lower than 6.3, and separating the precipitate, and converting the separated precipitate to 2,6-naphthalene dicarboxylic acid.

Canadian Patent 864587 discloses a process for the preparation of 2,6-NDA which comprises heating a monoalkali salt of 2,6-NDA in water or water-containing organic solvent causing disproportionation thereof into 2,6-NDA and a dialkali salt and separating the 2,6-NDA by a method that includes dissolving a rearrangement reaction product containing dialkali salt of 2,6-naphthalene dicarboxylic acid in warm water, filtering off the insoluble matter therefrom, concentrating the remaining solution, whereby the filtrate is concentrated to such a degree that the precipitation yield of the dialkali salt precipitated when the concentrated liquid is cooled to room temperature reaches at least 70% and the purity of said precipitate exceeds 99%, passing gaseous carbon dioxide through the aqueous solution of the precipitate recovered from the concentrated liquid, and recovering the resulting precipitate, and the mother liquour containing the side product dialkali salt of 2,6-naphthalene dicarboxylic acid is recycled into the carbon dioxide reaction step.

U.S. Pat. No. 5,175,354 discloses a reaction step wherein 2,6-naphthalene dicarboxylic acid potassium salts are allowed to react with benzene-carboxylic acids in the presence of water to yield 2,6-NDA and benzene-carboxylic acid potassium salts and a separation step wherein the crystallized 2,6-NDA is separated from the benzene-carboxylic acid potassium salts dissolved in the aqueous solution and provides 2,6-NDA.

None of these references suggest the idea of incorporating reverse osmosis membranes into a process for purifying 2,6-NDA.

There is a need in the art for alternative methods of separating the desired product and efficiently recycling byproducts. The purification process of the present invention provides an efficient way of separating and recycling byproducts which is advantageous.

SUMMARY OF THE INVENTION

In accordance with the foregoing the present invention comprises a process for purifying 2,6-naphthalene dicarboxylic acid produced by disproportionation and more efficiently recycling byproduct dipotassium salts which comprises:

a) Dissolving the disproportionation product of potassium naphthoate comprising the dipotassium salt of 2,6-NDA (K2NDA) in water, removing any residual disproportionation reaction medium, centrifuging the solution to remove the disproportionation catalyst, and removing acid salts other than 2,6-NDA by crystallization and/or carbon adsorption;

b) Contacting said aqueous solution of 2,6-K2NDA with carbon dioxide to form as a precipitate the monopotassium salt of 2,6-NDA (KHNDA) and an aqueous solution containing 2,3-KHNDA, K2NDA, and potassium bicarbonate;

c) Separating said monopotassium salt as a solid from said stream containing 2,3-KHNDA, K2NDA and potassium bicarbonate;

d) Disproportionating said monopotassium salt (KHNDA) to form solid 2,6-NDA and an aqueous solution containing K2NDA and potassium bicarbonate;

e) Separating said 2,6-NDA;

f) Concentrating said aqueous solution containing K2NDA and potassium bicarbonate from step (d) by reverse osmosis; and e) Recycling concentrated K2NDA to step (b) and pure water to step (d).

BRIEF DESCRIPTION OF THE DRAWING

The drawing is a process flow diagram illustrating the use of the process of the present invention as part of an integrated process for producing 2,6-naphthalene dicarboxylic acid.

DETAILED DESCRIPTION OF THE INVENTION

The novel process of the present invention for producing high purity 2,6-NDA begins with a disproportionation reaction product. This type reaction is described, for example, in U.S. Pat. Nos. 2,823,231 and 2,849,482.

The present invention is advantageously used in conjunction with a process for the production of 2,6-NDA by disproportionation of potassium naphthoate as described in copending U.S. Patent Application Ser. No. 60/151,577 (Attorney's Docket #TH1432), incorporated by reference herein in the entirety. In that application the disproportionation effluent solids (in naphthalene) consist primarily of 2,6 K2NDA, 2,3 K2NDA (isomer intermediate), unreacted KNA, catalyst, and trace coke. After leaving the disproportionation reactor the solvent is flashed.

Next, the solid product comprising dipotassium salts of 2,6-NDA, K2NDA (2,6-and 2,3-isomers), unreacted KNA, catalyst, heavy by-products, any residual solvent, and trace coke enter a water wash. The organic salts are dissolved and the liquid is directed to a decanter and centrifuge to remove residual solvent, catalyst and coke particles. The ZnO catalyst is regenerated and recycled.

The next step in the process is crystallization of the dipotassium salt. The dipotassium salt of naphthalene dicarboxylic acid resulting from the disproportionation reaction contains at least 15% unconverted feed and intermediates. The liquid carrying the dipotassium salts of NDA, K2NDA (2,6-and 2,3-isomers), KHCO$_3$, and unreacted KNA, flows to a two-stage evaporative crystallization section, where the disalt of 2,6 NDA (2,6 K2NDA) is selectively precipitated.

The crystallization section rejects a mother liquor stream containing KHCO$_3$, unreacted KNA, and 2,3 K2NDA. Recovery of 2,6 K2NDA is approximately 90%, and the purity of the K2NDA leaving the second crystallizer is 99.9%+.

The purified K2NDA slurry is then redissolved with additional clean water and optionally treated with a solid adsorbing agent. Examples of solid adsorbing agents include activated carbon, alumina, magnesia or ion exchange resins. The use of activated carbon is especially preferred. The amount of the solid adsorbent to be used depends upon the amounts of impurities contained therein. A suitable amount of adsorbent would be in the range of 0.1 to 10 percent by weight, preferably 0.5 to 5 percent by weight, based on the K2NDA. By subjecting an aqueous solution of the dipotassium salt to a solid adsorbent, most residual trace impurities that could affect the color of the final product can be removed.

Next, the monopotassium salt of 2,6-NDA (KHNDA) is selectively precipitated from an aqueous solution of K2NDA (about 20%) by reacting said aqueous solution at 0–200 psi $CO_2$ pressure, and 0–50° C. for about 30 minutes. The reaction produces the solid mono-potassium salt of 2,6-NDA, 2,6-KHNDA, and also 2,3-KHNDA and potassium bicarbonate. 2,3-KHNDA is rejected from the 2,6-KHNDA crystals.

The $CO_2$ precipitation step effectively separates 2,6-KHNDA from 2,3-KHNDA, which remains in solution due to its higher solubility. Examples 1–8 demonstrate this separation. The rejection of the 2,3-KHNDA is beneficial because, as a result, 2,3-KHNDA does not interfere with the separation of the 2,6-NDA from the K2NDA and the reverse osmosis of the present invention that takes place after the disproportionation of the 2,6-KHNDA.

Yields of 2,6-KHNDA better than 80% have been demonstrated at only 1 atm $CO_2$ pressure. The fact that the precipitation can be done effectively at modest pressure allows for centrifugation of the product without releasing pressure. The centrate also contains dissolved potassium bicarbonate and 2,3-KHNDA.

KHNDA solids are then diluted to 5–10% and disproportionated by reacting for less than an hour, preferably about 20 to 30 minutes at 150° C., under about 50 Psi $CO_2$ pressure. The reactor effluent from this step is separated to give a 2,6-NDA solid, and a centrate containing predominantly 2,6-K2NDA and KHCO$_3$.

This centrate stream from the disproportionation of the monosalt, KHNDA, is the primary focus of the present invention. According to the present invention the K2NDA in the centrate stream would be very useful if recycled to the $CO_2$ precipitation step, however it has to be concentrated because the optimal salt concentration in the CO2 precipitation step is about 20 wt %, whereas it is less than 10 wt % in the KHNDA disproportionation step. Concentrating this solution by evaporating off water is very energy intensive and costly.

It has been discovered in the present invention that when the solid 2,6-NDA produced in the disproportionation of KHNDA is separated out, the remaining solution containing K2NDA and potassium bicarbonate can be concentrated via reverse osmosis and recycled to the $CO_2$ precipitation step very efficiently and economically. The reverse osmosis step produces a pure water stream that can be recycled to the disproportionation step, and a concentrated K2NDA solution that can be recycled to the $CO_2$ precipitation step. Any potassium present in forms such as potassium carbonate or potassium bicarbonate is also separated by the membrane for recycle.

The dipotassium salt should be concentrated to a wt % in the range of 10–30 wt % salt. In the examples of the present invention the target was 20 wt % salt.

The reverse osmosis membranes that are suitable for use in the process are those characterized by high flux and high salt rejection, hydrolytic stability, resistance to compaction under pressure, and resistance to chemical attack.

The membranes employed in the examples were thin film composite membranes. These membranes consist of three layers: a support web, a microporous polysulfone layer with controlled pore diameters, and an ultrathin polyamide coating which is the selective layer. The support web provides the major structural support; the interlayer provides a smooth surface for the selective layer. The selective layer is on the order of 0.2 microns and can withstand high pressures due to the support provided by the interlayer. Examples of suitable membranes are FT-30 and HP-31, commercially available from Rochem Environmental, Inc.

In the present invention it is necessary to increase pressure in conjunction with the use of the membranes to achieve the desired concentration of the K2NDA. Suitable pressure is a pressure higher than the osmotic pressure of the solution. Good results were observed where a pressure in the range of 800 to 2000 psig was used. In some cases it is advantageous to use a pressure on the lower end of the range until most of the water is recovered, say 60–80%, and then employ a higher pressure. Examples 9–13 and 14–19 set forth data obtained for tests at low pressure and two-stage (low to high) pressure, respectively.

It has been found that the 2,6-NDA produced by this process is of high purity and contains only low levels of potassium. It has also been found that potassium can be removed to even lower levels by washing the 2,6-NDA with water.

DETAILED DESCRIPTION OF THE DRAWING

The drawing is a flow diagram showing one embodiment of the process of the present invention as part of a purification section for producing 2,6-NDA. It is understood the drawing is only intended as an illustration and not intended to limit the scope of the invention.

Referring to the FIGURE, solid product comprising dipotassium salts of NDA, K2NDA (2,6 and 2,3 isomers), unreacted KNA, catalyst, heavy by-products, and trace coke from which most of the reaction medium from the disproportionation reaction has been removed, represented by 1 enters water wash 2 where the organic salts are dissolved. Steam and 25% naphthalene can enter the water wash via 3 from another section of the process. The entire integrated process is discussed in detail in copending Ser. No. 60/151, 577 (Attorney's Docket #TH1432), incorporated by reference herein in its entirety. The liquid is then directed to a decanter 4 to remove any residual solvent, catalyst and coke particles. Naphthalene and some solids exit the process at 5, while an aqueous solution of crude K2NDA also containing solid ZnO catalyst is directed to a centrifuge 6. ZnO catalyst exits the centrifuge through 7 and is recycled. The liquid carrying the mixed organic salts, including the crude K2NDA is directed through 8 to a two-stage evaporative crystallization section, 9 and 10.

In the evaporative crystallization section 2,6-K2NDA is selectively precipitated from crude K2NDA product, rejecting KNA, 2,3-K2NDA, and $KHCO_3$. First, the crude K2NDA stream 8 and a recycle stream 11 containing $KHCO_3$ are added to evaporative crystallizer 9. In evaporative crystallizer 9, 2,6-K2NDA is selectively precipitated as water is evaporated. The water vapor exits the crystallizer, and is condensed by overhead exchanger 12. The water is then routed through line 13 to other portions of the finishing section in order to provide a dilution medium. The contents of the first evaporative crystallizer 9 exit through 14 to centrifuge 15. In centrifuge 15, mother liquor containing KNA, 2,3-K2NDA, and $KHCO_3$ are rejected, exit at 16, and are recycled back to the salt formation reactor in another section of the integrated process. The K2NDA solids are combined with recycle stream 17 containing $KHCO_3$ and 2,6-K2NDA and added to the second stage evaporative crystallizer 10. In 10 2,6-K2NDA is again selectively precipitated as water evaporates and exits the crystallizer. The water is condensed by overhead exchanger 18 and is directed into line 13. The purified K2NDA slurry leaves the second stage evaporative crystallizer through 19 and is directed to centrifuge 20. In centrifuge 20 mother liquor containing $KHCO_3$ is separated from purified 2,6-K2NDA and recycled back to the first stage evaporative crystallizer 9 through 11.

The purified solid 2,6-K2NDA is dissolved with water from overhead line 13 and transported through line 21 to an activated carbon guard bed 22. The 2,6-K2NDA solution then passes through the activated carbon guard bed 22 to remove residual trace impurities that could affect the color of the final product.

The 2,6-K2NDA solution exits the activated carbon bed 22 via line 23 and is directed to the $CO_2$ precipitation reactor 24. $CO_2$ is added to reactor 24 through line 25. In reactor 24 the monopotassium salt of 2,6-NDA, KHNDA, is selectively precipitated from the 2,6-K2NDA solution. The KHNDA is then directed out of the reactor through line 26 to centrifuge 27. The mother liquor, containing $KHCO_3$ and unreacted 2,6-K2NDA, is separated from the solid KHNDA and is recycled back to the second stage evaporative crystallizer 10 via line 17. The solid KHNDA is slurried with water from recycle line 28 and directed through line 29 to disproportionation reactor 30. $CO_2$ is added to reactor 30 through line 31. The KHNDA is reacted in the presence of 50 psig $CO_2$ and about 150° C. in disproportionation reactor 30 to form solid 2,6-NDA and 2,6-K2NDA. The reactor effluent from this step is directed through 32 to centrifuge 33.

This is the point where the present invention provides a very efficient method of making the process more economical. The solid 2,6-NDA is separated from the mother liquor and exits through 35 to a section for further purification and reduction of potassium levels. The centrate containing predominantly 2,6-K2NDA is directed through 34 to a two-stage reverse osmosis section, 36 & 38. In 36 the K2NDA feed enters a reverse osmosis stage operated at a lower pressure. Concentrate exits at 37 and is directed to a second reverse osmosis stage 38 operated at higher pressure, and permeate (water) exits at 39 and connects with a water recycle line which is directed back to the disproportionation step. The concentrate from 38 exits into line 25 which recycles back to the $CO_2$ precipitation step and water from the second stage reverse osmosis exits at 40.

The present invention will be more clearly understood from the following examples. It is understood that these examples are presented only to illustrate some embodiments of the invention and are not intended to limit the scope thereof.

EXAMPLES 1–8

Examples 1–8 were performed to investigate the separation of 2,3-KHNDA from 2,6-KHNDA in the $CO_2$ precipitation step. In these experiments, aqueous solutions containing 5% molar 2,3-K2NDA based on 2,6-K2NDA were contacted with $CO_2$ at 100° C. and various $CO_2$ pressures. The results in Table 1 show that the precipitate obtained by this process contained essentially no 2,3-NDA impurity.

TABLE 1

(Separation of 2,3 - NDA from 2,6 - NDA)

| | Ex. 1 | Ex. 2 | Ex. 3 | Ex. 4 | Ex. 5 | Ex. 6 | Ex. 7 | Ex. 8 |
|---|---|---|---|---|---|---|---|---|
| Initial solution weight (g) | 50 | 50 | 59 | 52 | 50 | 50 | 50 | 52 |
| % K2NDA in initial solution | 20 | 20 | 20 | 20 | 20 | 20 | 20 | 20 |
| 2,3/2,6 molar ratio | 0.05 | 0.05 | 0.05 | 0.05 | 0.05 | 0.05 | 0.05 | 0.05 |
| $CO_3$/2,6 molar ratio | 0.15 | 0.15 | 0.15 | 0.15 | 0.15 | 0.15 | 0.15 | 0.15 |
| $CO_2$ pressure (psig) | 400 | 400 | 400 | 400 | 200 | 200 | 200 | 200 |
| Contact time (hr) | 1 | 1 | 1 | 1 | 1 | 1 | 1 | 1 |
| Temperature (° C.) | 100 | 100 | 100 | 100 | 100 | 100 | 100 | 100 |
| Precipitate weight (g) | 6.5 | 7.48 | 6.5 | 7.6 | 5.41 | 5.23 | 4.95 | 6.58 |
| 2,6 - NDA in precipitate (% w) | 80.8 | 78 | 79 | 79.8 | 79.5 | 79.5 | 80.2 | 80.1 |
| 2,3 - NDA in precipitate (ppm) | 135 | 160 | 125 | <60 | <60 | <60 | <60 | 45 |
| K in precipitate (% w) | 13.7 | 14.9 | 14.5 | 13.8 | 14.2 | 14.2 | 13.6 | 14 |
| 2,3/2,6 molar ratio in product | $2 \times 10^{-4}$ | $2 \times 10^{-4}$ | $2 \times 10^{-4}$ | $<8 \times 10^{-5}$ | $<8 \times 10^{-5}$ | $<8 \times 10^{-5}$ | $<8 \times 10^{-5}$ | $<6 \times 10^{-5}$ |

EXAMPLES 9–13

Reverse osmosis experiments were carried out using a 3 wt % solution of 2,6-K2NDA. The pH and conductivity of the test solution were 9.2 and 16,100 μS/cm, respectively. A Rochem Disc Tube™(DT) module, scaled down to $1/6^{th}$ of the standard 169 membrane module was used for all examples. Examples 9–13 were performed at low pressure using an FT30 membrane. In the low pressure test, the system was operated below 900 psig. Examples 14–19 were carried out using an FT-30 membrane in a low pressure module and an HP31 membrane in a high pressure module. The low pressure module was operated below 900 psig up to a 75% water recovery, and then a switch was made to the high pressure module operated below 1800 psig. The initial feed volume was 62 liters. Based on the calculated feed concentration of 3 wt %, a volume reduction requirement of 85% was assumed to achieve the goal of 20 wt % K2NDA in the resulting stream. The results obtained are set forth in Tables 2 and 3 and clearly show excellent salt rejection achieved. The flux rates obtained in these examples after normalization with respect to temperature and pressure range from about 25 to about 70 gal/sq. ft-day.

TABLE 2

(Results of low pressure reverse osmosis test)

| | Ex. 9 | Ex. 10 | Ex. 11 | Ex. 12 | Ex. 13 |
|---|---|---|---|---|---|
| % recovery | 0 | 25 | 50 | 75 | 85 |
| K2NDA in feed (ppm) | 28000 | 35000 | 53000 | 107000 | 155000 |
| K2NDA in permeate (ppm) | 30 | 37 | 58 | 99 | 264 |
| % rejection | 99.9 | 99.9 | 99.9 | 99.9 | 99.8 |
| Pressure (psig) | 500 | 525 | 525 | 750 | 850 |
| Flux (gal/sq. ft. - day) | 32.7 | 37.6 | 31.8 | 24.1 | 11.1 |
| Temperature (° F.) | 73 | 83 | 94 | 98 | 102 |

TABLE 3

(Results of low pressure/high pressure reverse osmosis test)

| | Ex. 14 | Ex. 15 | Ex. 16 | Ex. 17 | Ex. 18 | Ex. 19 |
|---|---|---|---|---|---|---|
| % recovery | 0 | 25 | 50 | 75 | 75 | 85 |
| K2NDA in feed (ppm) | 27000 | 35000 | 57000 | 103000 | 105000 | 178000 |
| K2NDA in permeate (ppm) | 59 | 81 | 168 | 399 | 151 | 495 |
| % rejection | 99.8 | 99.8 | 99.7 | 99.6 | 99.9 | 99.7 |
| Pressure (psig) | 500 | 525 | 525 | 680 | 1000 | 1400 |
| Flux (gal/sq. ft - day) | 27.5 | 30.3 | 26 | 18.8 | 37.6 | 23.1 |
| Temperature (° F.) | 76 | 90 | 94 | 102 | 106 | 115 |

We claim:

1. A process for purifying 2,6-naphthalene dicarboxylic acid comprising:
   a) dissolving a product remaining from the disproportionation of potassium naphthoate comprising a dipotassium salt of 2,6-naphthalene dicarboxylic acid in water to form an aqueous solution, removing any remaining disproportionation reaction medium, centrifuging the solution to separate disproportionation catalyst, and removing acid salts other than 2,6-naphthalene dicarboxylic acid by crystallization and/or carbon adsorption, b) Contacting said aqueous solution of the dipotassium salt of 2,6-naphthalene dicarboxylic acid with carbon dioxide to form as a precipitate a monopotassium salt of 2,6-naphthalene dicarboxylic acid and an aqueous solution containing a monopotassium salt of 2,3-naphthalene dicarboxylic acid, dipotassium salt of naphthalene dicarboxylic acid, and potassium bicarbonate;

c) Separating said monopotassium salt of 2,6-naphthalene dicarboxylic acid as a solid from said solution containing the monopotassium salt of 2,3-naphthalene dicarboxylic acid, dipotassium salt of 2,6-naphthalene dicarboxylic acid and potassium bicarbonate;

d) Disproportionating the monopotassium salt of 2,3-naphthalene dicarboxylic acid to form 2,6-naphthalene dicarboxylic acid and an aqueous solution containing the dipotassium salt of 2,6-naphthalene dicarboxylic acid, and potassium bicarbonate;

e) Separating said 2,6-naphthalene dicarboxylic acid;

f) Concentrating said aqueous solution containing 2,6-naphthalene dicarboxylic acid and potassium bicarbonate from step (d) by reverse osmosis; and g) Recycling concentrated 2,6-naphthalene dicarboxylic acid to step (b) and pure water to step (d).

2. The process of claim 1 wherein concentrating the aqueous solution containing 2,6-naphthalene dicarboxylic acid and potassium bicarbonate by reverse osmosis results in a disalt concentration of 10–30 wt % dipotassium naphthalene dicarboxylic acid.

3. The process of claim 2 wherein concentrating the aqueous solution containing 2,6-naphthalene dicarboxylic acid and potassium bicarbonate by reverse osmosis results in a disalt concentration of about 20 wt % dipotassium naphthalene dicarboxylic acid.

4. The process of claim 1 wherein concentrating said aqueous solution containing 2,6-naphthalene dicarboxylic acid and potassium bicarbonate by reverse osmosis is accomplished using thin film composite membranes.

5. The process of claim 4 wherein the membrane further comprises three layers consisting of a support web, a microporous polysulfone interlayer with controlled pore diameters, and an ultrathin polyamide coating selective layer.

6. The process of claim 5 wherein the selective layer is on the order of 0.2 microns and can withstand high pressures due to the support provided by the interlayer.

7. The process of claim 1 wherein concentrating the aqueous solution containing 2,6-naphthalene dicarboxylic acid and potassium bicarbonate by reverse osmosis is carried out under a pressure in the range of 500 to 2000 psig.

8. The process of claim 1 wherein concentrating the aqueous solution containing 2,6-naphthalene dicarboxylic acid and potassium bicarbonate by reverse osmosis is carried out in two stages.

9. The process of claim 8 further comprising contacting the solution of dipotassium salts with a reverse osmosis membrane at a pressure of about 500–900 psig for a period and then contacting the concentrate with a second reverse osmosis membrane at a pressure of about 1600–1800 psig for a period of time.

10. The process of claim 7 further comprising contacting the solution of dipotassium salts with the first membrane a pressure below 900 psig until about 70–80% of the water is recovered and then contacting the solution with the second membrane at a pressure below 1800 psig.

11. A novel process for producing high purity 2,6-naphthalene dicarboxylic acid which comprises:

a) Disproportionating potassium naphthoate to produce a disproportionation reactor effluent containing reaction medium and disproportionation reaction solids comprising isomers of the dipotassium salt of 2,6-NDA, unreacted feed, catalyst and trace coke, b) Removing naphthalene by flashing;

c) Dissolving said reaction solids in water;

d) Separating any residual solvent and the solid catalyst from the reaction mixture;

e) Adding aqueous potassium bicarbonate to the mixture of aqueous potassium salts and evaporating a portion of the water to selectively crystallize the dipotassium salt of 2,6-naphthalene dicarboxylic acid as a solid and separating said solid;

f) Removing acid salts other than the salts of 2,6-NDA by crystallization and, optionally, carbon adsorption;

g) Dissolving said dipotassium salt of 2,6-naphthalene dicarboxylic acid in water;

h) Contacting said aqueous dipotassium salt of 2,6-naphthalene dicarboxylic acid with carbon dioxide to create a mixture of solid monopotassium salt of 2,6-naphthalene dicarboxylic acid and aqueous potassium bicarbonate, and separating said solids from the aqueous solution;

i) Contacting solid monopotassium salt of 2,6-NDA with water, optionally in the presence of carbon dioxide, to form solid 2,6-naphthalene dicarboxylic acid, aqueous dipotassium salt of 2,6-naphthalene dicarboxylic acid, and potassium bicarbonate;

j) Separating the solid 2,6-naphthalene dicarboxylic acid;

k) Concentrating said aqueous solution by reverse osmosis and recycling to the crystallization step (e).

* * * * *

UNITED STATES PATENT AND TRADEMARK OFFICE
CERTIFICATE OF CORRECTION

PATENT NO.   : 6,562,999 B2
DATED        : May 13, 2003
INVENTOR(S)  : Zaida Diaz and John B. Rodden It is certified that error appears in the above-identified patent and that said Letters Patent is hereby corrected as shown below:

<u>Column 10,</u>
Line 11, "claim 7" should read -- claim 9 --.

Signed and Sealed this

Second Day of September, 2003

JAMES E. ROGAN
*Director of the United States Patent and Trademark Office*